US009933333B2

United States Patent
Kawada et al.

(10) Patent No.: US 9,933,333 B2
(45) Date of Patent: Apr. 3, 2018

(54) BEARING DIAGNOSTIC DEVICE FOR MACHINE TOOL

(71) Applicant: Okuma Corporation, Niwa-Gun (JP)

(72) Inventors: Naoki Kawada, Niwa-Gun (JP); Issei Koike, Niwa-Gun (JP)

(73) Assignee: Okuma Corporation, Niwa-Gun (JP)

( * ) Notice: Subject to any disclaimer, the term of this patent is extended or adjusted under 35 U.S.C. 154(b) by 130 days.

(21) Appl. No.: 15/209,817

(22) Filed: Jul. 14, 2016

(65) Prior Publication Data

US 2017/0067796 A1  Mar. 9, 2017

(30) Foreign Application Priority Data

Sep. 7, 2015 (JP) ................. 2015-175959

(51) Int. Cl.
| | |
|---|---|
| B21D 53/10 | (2006.01) |
| B21K 1/76 | (2006.01) |
| B23P 17/00 | (2006.01) |
| G01M 13/04 | (2006.01) |
| G01K 13/08 | (2006.01) |
| F01M 1/16 | (2006.01) |

(Continued)

(52) U.S. Cl.
CPC ............ *G01M 13/04* (2013.01); *F01M 1/16* (2013.01); *F16C 33/6637* (2013.01); *F16N 29/04* (2013.01); *G01K 13/08* (2013.01); *F16N 2250/08* (2013.01); *F16N 2250/16* (2013.01); *F16N 2270/52* (2013.01); *G01N 11/14* (2013.01); *G01N 19/02* (2013.01)

(58) Field of Classification Search
USPC .................................. 29/898.09
See application file for complete search history.

(56) References Cited

U.S. PATENT DOCUMENTS

| | | | | |
|---|---|---|---|---|
| 2,937,518 A | * | 5/1960 | Hochheiser | G01M 13/04 73/9 |
| 3,078,711 A | * | 2/1963 | Shutt | G01M 13/02 464/4 |

(Continued)

FOREIGN PATENT DOCUMENTS

| | | |
|---|---|---|
| JP | 06-65189 B2 | 8/1994 |
| JP | 4091885 B2 | 5/2008 |
| JP | 2009-020090 A1 | 1/2009 |

*Primary Examiner* — Clayton E Laballe
*Assistant Examiner* — Warren K Fenwick
(74) *Attorney, Agent, or Firm* — Burr & Brown, PLLC

(57) ABSTRACT

A bearing diagnostic device senses a failure in a bearing of a machine tool including a rotation shaft device. The bearing diagnostic device includes a rotation counting unit, a temperature measuring unit, a frictional torque calculating unit, a rolling speed calculating unit, a bearing characteristic calculating unit, a storage unit, and a determination unit. The frictional torque calculating unit is configured to calculate a frictional torque of the rotation shaft device. The rolling speed calculating unit is configured to calculate a rolling speed of the bearing from the count of rotations. The bearing characteristic calculating unit is configured to calculate a bearing characteristic from the frictional torque and the rolling speed. The determination unit is configured to compare the bearing characteristic calculated by the bearing characteristic calculating unit with a reference bearing characteristic stored in the storage unit to determine a presence of a failure.

9 Claims, 3 Drawing Sheets

(51) Int. Cl.
    *F16C 33/66*     (2006.01)
    *F16N 29/04*     (2006.01)
    *G01N 11/14*     (2006.01)
    *G01N 19/02*     (2006.01)

(56) References Cited

U.S. PATENT DOCUMENTS

| | | | | |
|---|---|---|---|---|
| 3,146,619 | A * | 9/1964 | Sinclair | G01L 5/28 |
| | | | | 73/116.01 |
| 5,167,148 | A * | 12/1992 | Black | G01L 5/28 |
| | | | | 73/121 |
| 8,782,902 | B2 * | 7/2014 | Pyun | B24B 35/00 |
| | | | | 29/898.13 |
| 8,967,864 | B2 * | 3/2015 | Koike | B23Q 1/70 |
| | | | | 384/519 |

* cited by examiner

BEARING DIAGNOSTIC DEVICE FOR MACHINE TOOL

This application claims the benefit of Japanese Patent Application Number 2015-175959 filed on Sep. 7, 2015 the entirety of which is incorporated by reference.

BACKGROUND

Technical Field

This disclosure relates to a bearing diagnostic device to sense failures in a rolling bearing used for pivotally supporting a rotation shaft in a machine tool.

Related Art

A rotation shaft device, which includes a rotation shaft such as a main spindle and is disposed in a machine tool, includes a rolling bearing (hereinafter simply referred to as a "bearing") used to pivotally support the rotation shaft. The rolling bearing includes an inner race, an outer race, a plurality of rolling elements (such as balls and rollers), which are disposed between both races, and a retainer to keep an interval of the rolling elements. The inner race integrally rotates with the rotation shaft, and the outer race is embedded into a main spindle housing or a similar member and is secured.

Failures that occur in this bearing include a lubrication failure, an entrance of a foreign matter, a friction, an excessive load, and a similar failure. These failures cause a rotation failure and a burn-out, resulting in obstructing a normal operation of the machine tool. Therefore, it is preferable to diagnose the bearing for failure.

Japanese Patent No. 4091885 (hereinafter referred to as Patent document 1) discloses a method for diagnosing a failure in a bearing. In the method, a temperature and a stop time of a rotating device having the bearing are monitored and the stop time is compared with a reference stop time preset corresponding to a temperature so as to determine a presence/absence of a failure in the bearing. Japanese Unexamined Patent Application Publication No. 2009-20090 (hereinafter referred to as Patent document 2) discloses the following. Sounds and vibrations during operation are detected for frequency analysis. Through a comparison with a frequency spectrum level of a preset abnormal frequency, a determination for failure is performed. Furthermore, Japanese Published Examined Application 6-65189 (hereinafter referred to as Patent document 3) discloses the following. A frictional torque is calculated from a change in the count of rotations during an inertial rotation of a shaft and the frictional torque is compared with a reference value so as to determine the presence of a failure in the bearing.

With the disclosure of Patent document 1, in the case where a temperature rise in the bearing is monitored at the main spindle of the machine tool, especially a machining center, there is no choice but to install a temperature sensor to a structure near the bearing. This only results in indirect temperature measurement, thereby failing to observe a rapid change in the bearing temperature. Additionally, the accuracy of observation depends on performance of the temperature sensor itself. Therefore, there is a possibility that a failure in the bearing is not noticed, resulting in a damage of the machine.

With the disclosure of Patent document 2, a bearing failure is accurately sensable through the analysis of sounds and vibrations. However, this requires expensive measuring devices such as a vibration sensor and a sound sensor, leading to a cost increase.

With the disclosure of Patent document 3, a rate of the change in the count of rotations during the inertial rotation of the shaft is converted to obtain the frictional torque, therefore, it cannot be said that the frictional torque is accurate. In addition, the calculated frictional torque is simply compared with the reference value so as to determine the presence of the failure in the bearing, therefore, it cannot be said that accuracy of determination is high.

An object of this disclosure is to provide a bearing diagnostic device for a machine tool that can accurately diagnose a presence of a failure in a bearing at an early phase at which a damage of a machine is avoided inexpensively.

SUMMARY

In order to achieve the above-described object, there is provided a bearing diagnostic device for a machine tool according to a first aspect of the disclosure. The bearing diagnostic device for the machine tool is for sensing a failure in a bearing of a rotation shaft device in a machine tool. The bearing pivotally supports a rotation shaft to be rotatably driven in the rotation shaft device. The bearing diagnostic device for the machine tool includes a rotation counting unit, a temperature measuring unit, a frictional torque calculating unit, a rolling speed calculating unit, a bearing characteristic calculating unit, a storage unit, and a determination unit. The rotation counting unit is configured to measure a count of rotations of the rotation shaft at a specific rotation speed. The temperature measuring unit is configured to measure a temperature of the rotation shaft device. The frictional torque calculating unit is configured to calculate a frictional torque of the rotation shaft device. The rolling speed calculating unit is configured to calculate a rolling speed of the bearing from the count of rotations. The bearing characteristic calculating unit is configured to calculate a bearing characteristic from the frictional torque and the rolling speed. The storage unit stores a reference bearing characteristic. The determination unit is configured to compare the bearing characteristic calculated by the bearing characteristic calculating unit with the reference bearing characteristic stored in the storage unit to determine a presence of a failure.

In the bearing diagnostic device for the machine tool according to a second aspect of the disclosure, which is in the first aspect of the disclosure, the rotation counting unit is configured to measure a count of rotations from when the rotation shaft is at the specific rotation speed until the rotation shaft stops.

In the bearing diagnostic device for the machine tool according to a third aspect of the disclosure, which is in the first or the second aspect of the disclosure, the temperature measuring unit is configured to measure a temperature from when the rotation shaft is at the specific rotation speed until the rotation shaft stops.

In the bearing diagnostic device for the machine tool according to a fourth aspect of the disclosure, which is in any one of the first to the third aspects of the disclosure, the bearing characteristic calculating unit is configured to add a bearing preload and a lubricating oil viscosity to the frictional torque and the rolling speed to calculate the bearing characteristic.

In the bearing diagnostic device for the machine tool according to a fifth aspect of the disclosure, which is in the fourth aspect of the disclosure, the bearing preload is obtained by preload estimating unit. The preload estimating unit is configured to estimate the bearing preload from a relationship between the temperature and the count of rotations.

In the bearing diagnostic device for the machine tool according to a sixth aspect of the disclosure, which is in the fourth or the fifth aspect of the disclosure, the lubricating oil viscosity is obtained by lubricating oil viscosity estimating unit. The lubricating oil viscosity estimating unit is configured to estimate the lubricating oil viscosity from a relationship between the temperature and the count of rotations.

In the bearing diagnostic device for the machine tool according to a seventh aspect of the disclosure, which is in any one of the first to the sixth aspects of the disclosure, the frictional torque calculating unit is configured to calculate the frictional torque by a formula for computation using the count of rotations, a moment of inertia, and an acceleration.

In the bearing diagnostic device for the machine tool according to an eighth aspect of the disclosure, which is in any one of the first to the seventh aspects of the disclosure, the rolling speed calculating unit is configured to calculate the rolling speed by a formula for computation using the count of rotations, a rolling bearing pitch circle diameter, a rolling bearing diameter, and a contact angle.

The bearing diagnostic device for the machine tool according to a ninth aspect of the disclosure, which is in any one of the first to the eighth aspects of the disclosure, further includes notification unit configured to notify a determination result by the determination unit.

With the embodiment, the bearing characteristic is calculated from the frictional torque and the rolling speed and is compared with the reference bearing characteristic to determine a presence of a failure. Thus, the presence of the failure in the bearing is accurately diagnosed at an early phase at which a damage of a machine is avoided inexpensively.

DETAILED DESCRIPTION

The following describes an embodiment according to the disclosure based on the drawings.

Figure 1:
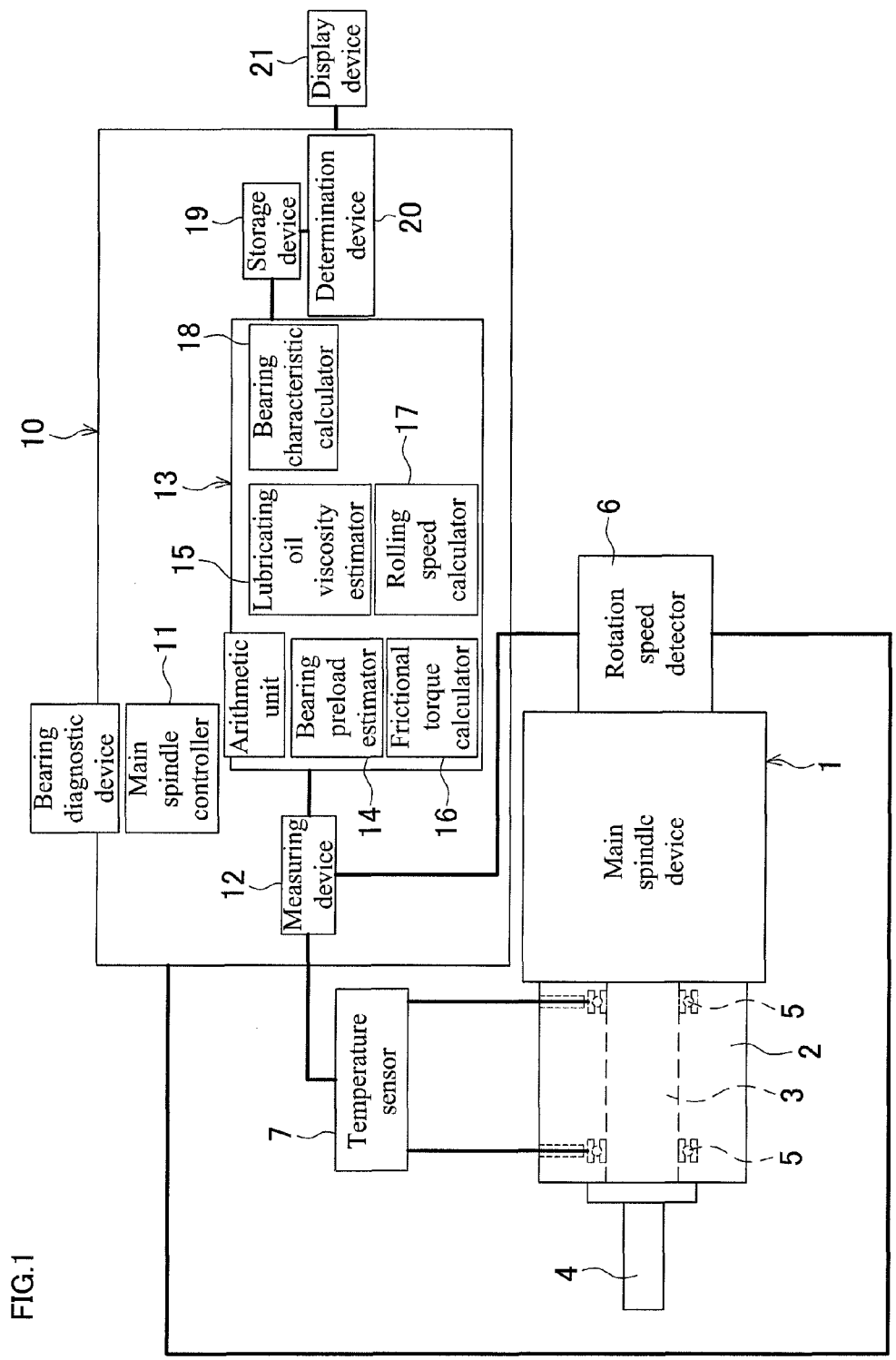
FIG. 1 is a schematic diagram of a bearing diagnostic device for a machine tool.

FIG. 1 is a schematic diagram illustrating an example of a bearing diagnostic device for a machine tool. This bearing diagnostic device diagnoses a bearing used for a main spindle device as a rotation shaft device, which rotates a tool.

In FIG. 1, 1 donates a main spindle device. In a main spindle housing 2, bearings (here, ball bearings whose rolling elements are balls) 5 and 5 pivotally support a main spindle 3 as a rotation shaft. A tool 4 is mounted to a distal end of the main spindle 3 and is rotated by a main spindle motor (not illustrated). A rotation speed detector 6 detects a rotation speed of the main spindle 3. The main spindle housing 2 includes a temperature sensor 7 from which probes are inserted to parts close to the bearings 5 and 5.

A bearing diagnostic device 10 includes a main spindle controller 11, which controls the main spindle motor, a measuring device 12, and an arithmetic device 13. A rotation detection signal from the rotation speed detector 6 and a temperature detection signal from the temperature sensor 7 are input to the measuring device 12. The count of rotations and a temperature are input to the arithmetic device 13. These rotation speed detector 6 and measuring device 12 serve as rotation counting unit, and the temperature sensor 7 and the measuring device 12 serve as temperature measuring unit.

The arithmetic device 13 includes a bearing preload estimator 14 as preload estimating unit, a lubricating oil viscosity estimator 15 as lubricating oil viscosity estimating unit, a frictional torque calculator 16 as frictional torque calculating unit, a rolling speed calculator 17 as rolling speed calculating unit, and a bearing characteristic calculator 18 as bearing characteristic calculating unit. The bearing preload estimator 14 estimates a preload of the bearing 5 from a temperature and the count of rotations of the bearing 5, which are obtained from the measuring device 12. The lubricating oil viscosity estimator 15 estimates viscosity of lubricating oil supplied to the bearing 5 from these temperature and count of rotations. The frictional torque calculator 16 calculates the frictional torque from the count of rotations of the main spindle 3, which is obtained from the measuring device 12. The rolling speed calculator 17 calculates a rolling speed of the bearing 5 from this count of rotations. The bearing characteristic calculator 18 calculates a bearing characteristic from the preload, the lubricating oil viscosity, the rolling speed, and the frictional torque of the bearing 5.

A storage device 19 is used as storage unit to store the bearing characteristic, which is used as a determination reference. A determination device 20 as determination unit compares the bearing characteristic calculated by the bearing characteristic calculator 18 with the bearing characteristic stored in the storage device 19 to determine a presence of a bearing failure. A display device 21 as notification unit, which is disposed on an NC system for the machine tool, displays this determination result.

Figure 2:
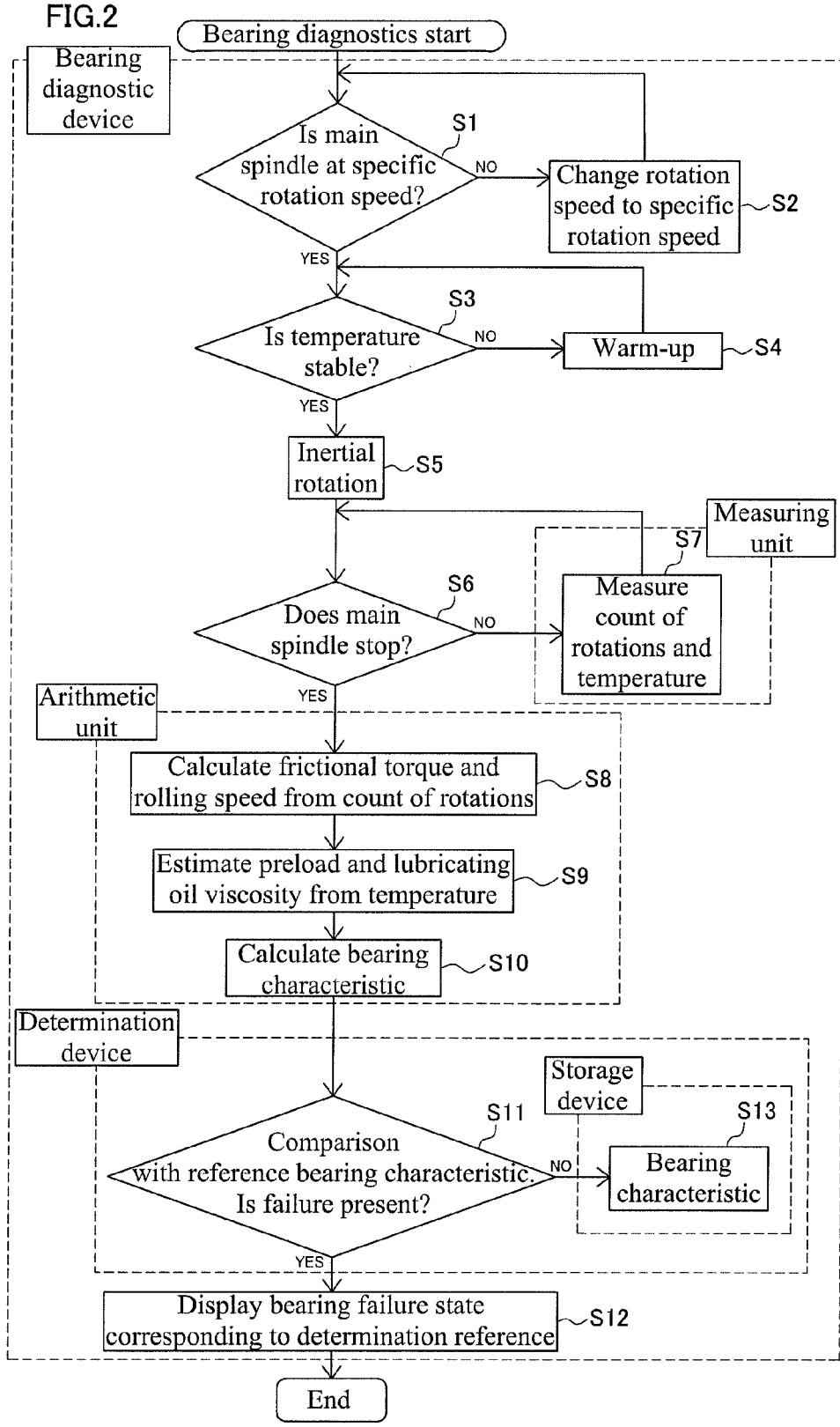
FIG. 2 is a flowchart of a procedure for a bearing diagnostics.

The following describes a procedure for a bearing diagnostics by the bearing diagnostic device 10 configured as described above with reference to the flowchart in FIG. 2.

When a command to start the diagnostics is input to the bearing diagnostic device 10, first, at S1, whether the main spindle 3 is at a specific rotation speed or not is judged. If not at the specific rotation speed, the main spindle controller 11 changes the speed to the specific rotation speed at S2. After a confirmation that the speed is at the specific rotation speed again at S1, whether a detected temperature, which is obtained from the temperature sensor 7, is stable (a steady state) or not is judged at S3. This steady state means that the detected temperature does not vary by a predetermined range or more in a predetermined time. In the case where the detected temperature is unstable, a warm-up operation targeting the predetermined temperature is performed at S4.

After a confirmation that the temperature is stable at S3 as a result of the warm-up operation, an energization to the main spindle motor is stopped and an inertial rotation is performed at S5. Until a stop of the main spindle 3 is confirmed at S6, the count of rotations and the temperature are measured at S7.

After the confirmation of the stop of the main spindle 3 at S6, in the arithmetic device 13, the frictional torque calculator 16 calculates the frictional torque and the rolling speed calculator 17 calculates the rolling speed at S8, based on the count of rotations, which is measured at S7. These frictional torque and rolling speed are calculated using the count of rotations and parameters preliminary stored in the storage device 19, such as, the following Expression 1, which uses the count of rotations, a moment of inertia, and an acceleration, and the following Expression 2, which uses the count of rotations, a ball pitch circle diameter, a ball diameter, and a contact angle. Expression 1 is a formula for computation of the frictional torque, and Expression 2 is a formula for computation of the rolling speed.

$$T = -\frac{2\pi M}{60} \cdot \frac{dV}{dt} \qquad \text{[Expression 1]}$$

T: Frictional torque, V: Count of rotations, M: Moment of inertia $$U_{front} = \frac{d^2 - D^2\cos^2\beta}{4d}\left(\frac{2\pi V}{60}\right) \qquad \text{[Expression 2]}$$

$U_{front}$: Rolling speed, V: Count of rotations, d: Ball pitch circle diameter D: Ball diameter, β: Contact angle Based on the temperature and the count of rotations measured at S7, the bearing preload estimator 14 estimates the bearing preload and the lubricating oil viscosity estimator 15 estimates lubricating oil viscosity at S9. This bearing preload is estimated by referring the measured temperature and count of rotations to a graph and a data table, which show a relationship between the temperature, the count of rotations, and the bearing preload, preliminary stored in the storage device 19. The lubricating oil viscosity is also estimated by referring the measured temperature and count of rotations to a graph and a data table, which show a relationship between the temperature, the count of rotations, and the lubricating oil viscosity, preliminary stored in the storage device 19.

Figure 3:
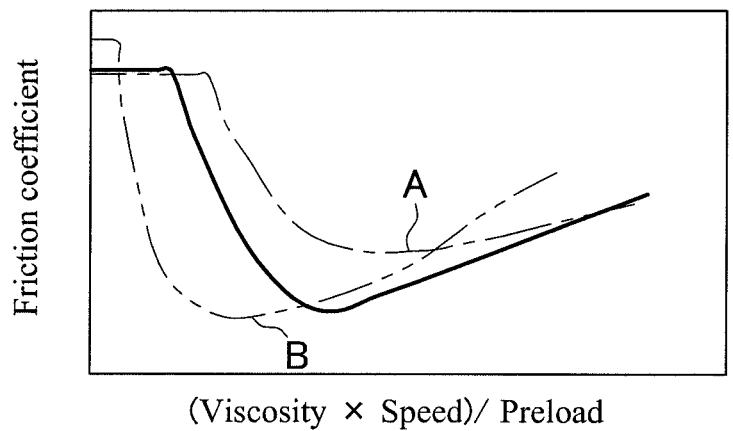
FIG. 3 is an explanatory view of a bearing characteristic (a Stribeck curve).

At S10, based on a relational expression of these calculation results, a frictional torque T, and a friction coefficient μ: T=μ×Pr×d/2 (Pr: radial load, d: bearing bore), the bearing characteristic (the Stribeck curve) indicative of a relationship between the friction coefficient and a bearing characteristic value as illustrated in FIG. 3 is calculated. In the bearing characteristic value, viscosity means lubricating oil viscosity, a speed means a rotation speed, and a preload means a bearing preload.

Next, at S11, the determination device 20 compares the reference bearing characteristic, which is preliminary stored in the storage device 19, with the bearing characteristic calculated at S10 to determine whether the failure has occurred or not.

For example, with a rough rolling surface of the ball that is indicated by one dot chain line A in FIG. 3, a difference appears in such a manner that the friction coefficient increases with respect to the normal bearing characteristic, which is indicated by a solid line. Therefore, when the friction coefficient increases by a predetermined value in a specific range, the determination device 20 determines that the failure has occurred in the bearing 5 (the lubrication failure). The determination result is displayed on the display device 21 at S12. Further, a failure in the preload is indicated by a two-dot chain line B in FIG. 3. A minimum part at a curved line part of the two-dot chain line B is shifted from that of the solid line, and an increase rate of the friction coefficient is different from that of the normal bearing characteristic at a relatively high bearing characteristic value. Accordingly, when the shift of the minimum part and the different increase rate of the friction coefficient can be confirmed, at S12, the determination device 20 determines that the failure has occurred in the bearing 5 (a preload loss) and the determination result is displayed on the display device 21.

Meanwhile, when the judgement at S11 turns out to be no failure in the bearing 5, the storage device 19 stores the calculated bearing characteristic at S13.

Thus, the bearing diagnostic device 10 according to the embodiment includes the rotation speed detector 6 and the measuring device 12, which are configured to measure the count of rotations of the main spindle 3 at the specific rotation speed, the temperature sensor 7 and the measuring device 12, which are configured to measure the temperature of the main spindle 3, the frictional torque calculator 16, which is configured to calculate the frictional torque of the bearing 5, the rolling speed calculator 17, which is configured to calculate the rolling speed of the bearing 5, the bearing preload estimator 14, which is configured to estimate the preload of the bearing 5, the lubricating oil viscosity estimator 15, which is configured to estimate the lubricating oil viscosity of the bearing 5, the bearing characteristic calculator 18, which is configured to calculate the bearing characteristic from the frictional torque, the rolling speed, the bearing preload, and the lubricating oil viscosity, the storage device 19, which stores the reference bearing characteristic, and the determination device 20, which is configured to compare the bearing characteristic calculated by the bearing characteristic calculator 18 with the reference bearing characteristic stored in the storage device 19 to determine the presence of the failure. With the above configuration, the presence of the failure in the bearing is accurately diagnosed at an early phase at which a damage of a machine is avoided inexpensively.

The configuration shows the example of the ball bearing as the bearing, however, the bearing may be a roller bearing. In addition to a notation of failure content of the bearing by characters, the display device may display the Stribeck curve illustrated in FIG. 3 together with the curved lines A and B in case of failure.

When there is no failure in the bearing characteristic calculated at S10, the bearing characteristic can be updated as the reference bearing characteristic, or an average bearing characteristic calculated from the several calculated bearing properties can be updated as the reference bearing characteristic.

Furthermore, the estimating method for the bearing preload by the preload estimating unit, the estimating method for the lubricating oil viscosity by the lubricating oil viscosity estimating unit, the calculation method for the frictional torque by the frictional torque calculating unit, the calculation method for the rolling speed by the rolling speed calculating unit, and a similar method are not limited to the above-described configurations, but are appropriately changeable.

With the configuration, the bearing characteristic is calculated from the frictional torque, the rolling speed, the bearing preload, and the lubricating oil viscosity. However, the bearing characteristic may be calculated only from the frictional torque and the rolling speed without the use of the bearing preload and the lubricating oil viscosity. Therefore, in this case, the preload estimating unit and the lubricating oil viscosity estimating unit can be omitted.

Meanwhile, the notification unit is not limited to the display device. A lamp, a synthetic sound, a buzzer sound, and a similar sound may be employed, or these sounds may be used in combination with the display device. However, the notification unit is omitted, only the storage device stores the failure content, and an operator can be called at a required timing.

The rotation shaft is not limited to the main spindle that causes the tool to rotate. The bearing diagnostics according to the disclosure is also applicable to a rotation shaft device that grips and rotates workpiece.

It is explicitly stated that all features disclosed in the description and/or the claims are intended to be disclosed separately and independently from each other for the purpose of original disclosure as well as for the purpose of restricting the claimed invention independent of the composition of the features in the embodiments and/or the claims. It is explicitly stated that all value ranges or indications of groups of entities disclose every possible intermediate value or intermediate entity for the purpose of original disclosure as well as for the purpose of restricting the claimed invention, in particular as limits of value ranges.

What is claimed is:

1. A bearing diagnostic device for sensing a failure in a bearing of a rotation shaft device in a machine tool, the bearing pivotally supporting a rotation shaft to be rotatably driven in the rotation shaft device, the bearing diagnostic device comprising:
    a rotation counting unit configured to measure a count of rotations of the rotation shaft at a specific rotation speed;
    a temperature measuring unit configured to measure a temperature of the rotation shaft device;
    a frictional torque calculating unit configured to calculate a frictional torque of the rotation shaft device;
    a rolling speed calculating unit configured to calculate a rolling speed of the bearing from the count of rotations;
    a bearing characteristic calculating unit configured to calculate a bearing characteristic from the frictional torque and the rolling speed;
    a storage unit storing a reference bearing characteristic; and
    a determination unit configured to compare the bearing characteristic calculated by the bearing characteristic calculating unit with the reference bearing characteristic stored in the storage unit to determine a presence of a failure.

2. The bearing diagnostic device for the machine tool according to claim 1, wherein
    the rotation counting unit is configured to measure a count of rotations from when the rotation shaft is at the specific rotation speed until the rotation shaft stops.

3. The bearing diagnostic device for the machine tool according to claim 1, wherein
    the temperature measuring unit is configured to measure a temperature from when the rotation shaft is the specific rotation speed until the rotation shaft stops.

4. The bearing diagnostic device for the machine tool according to claim 1, wherein
    the bearing characteristic calculating unit is configured to calculate the bearing characteristic from a bearing preload and a lubricating oil viscosity in addition to the frictional torque and the rolling speed.

5. The bearing diagnostic device for the machine tool according to claim 4, further comprising
    a preload estimating unit configured to estimate the bearing preload from a relationship between the temperature and the count of rotations to obtain the bearing preload.

6. The bearing diagnostic device for the machine tool according to claim 4, further comprising
    a lubricating oil viscosity estimating unit configured to estimate the lubricating oil viscosity from a relationship between the temperature and the count of rotations to obtain the lubricating oil viscosity.

7. The bearing diagnostic device for the machine tool according to claim 1, wherein
    the frictional torque calculating unit is configured to calculate the frictional torque by a formula for computation using the count of rotations, a moment of inertia, and an acceleration.

8. The bearing diagnostic device for the machine tool according to claim 1, wherein
    the rolling speed calculating unit is configured to calculate the rolling speed by a formula for computation using the count of rotations, a rolling bearing pitch circle diameter, a rolling bearing diameter, and a contact angle.

9. The bearing diagnostic device for the machine tool according to claim 1, further comprising
    a notification unit configured to notify a determination result by the determination unit.

* * * * *